United States Patent [19]

Englert et al.

[11] Patent Number: 5,476,850

[45] Date of Patent: Dec. 19, 1995

[54] AMINO-SUBSTITUTED BENZENESULFONYLUREAS AND -THIOUREAS AND THEIR USE AS PHARMACEUTICALS

[75] Inventors: Heinrich Englert, Hofheim; Dieter Mania, Königstein; Jens Hartung, Höchberg; Heinz Gögelein; Joachim Kaiser, both of Frankfurt, all of Germany

[73] Assignee: Hoechst Aktiengesellschaft, Frankfurt am Main, Germany

[21] Appl. No.: 353,263

[22] Filed: Dec. 5, 1994

[30] Foreign Application Priority Data

Dec. 7, 1993 [DE] Germany .................. 43 41 655.1

[51] Int. Cl.$^6$ .................. A61K 31/64; C07C 311/58; C07D 295/155

[52] U.S. Cl. .................. 514/239.5; 514/255; 514/331; 514/429; 514/584; 514/592; 514/227.5; 544/58.1; 544/159; 544/160; 544/393; 546/231; 548/577; 564/23; 564/41

[58] Field of Search .................. 564/23, 41; 544/159, 544/160; 546/231; 514/239.5

[56] References Cited

U.S. PATENT DOCUMENTS 3,998,968  12/1976  Hitzel et al. .

FOREIGN PATENT DOCUMENTS 1518879  8/1959  Germany .
1518874  7/1974  Germany .

OTHER PUBLICATIONS

Derwent Abstract of German Patent DE 1,518,874, Jul. 18, 1974.

L. H. Opie, "Modulation of Ischemia By Regulation Of The ATP-Sensitive Potassium Channel" Cardiovascular Drugs and Therapy, No. 7, pp. 507–513 (1993).

Primary Examiner—Robert W. Ramsuer
Attorney, Agent, or Firm—Finnegan, Henderson, Farabow, Garrett & Dunner

[57] ABSTRACT

There are described amino-substituted benzenesulfonylureas and -thioureas of the formula I

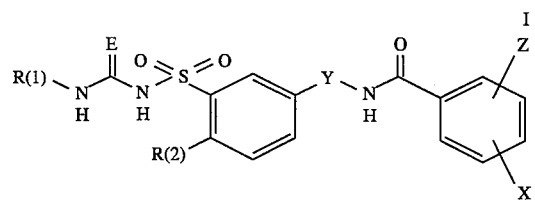

The compounds I are used for the treatment of cardiac arrhythmias and for the prevention of sudden heart death caused by arrhythmias and can therefore be used as antiarrhythmics. They are particularly suitable for those cases in which arrhythmias are a result of constriction of a coronary vessel, such as in angina pectoris or in acute cardiac infarct.

6 Claims, No Drawings

AMINO-SUBSTITUTED BENZENESULFONYLUREAS AND -THIOUREAS AND THEIR USE AS PHARMACEUTICALS

DESCRIPTION

Amino-substituted benzenesulfonylureas and -thioureas, processes for their preparation, and their use as pharmaceuticals The invention relates to substituted benzenesulfonylureas and -thioureas I

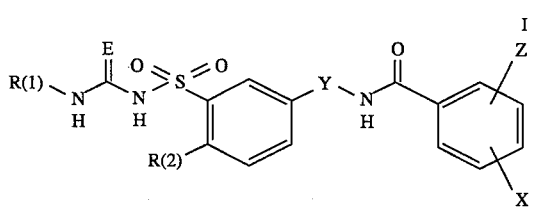

in which:
R(1) is hydrogen, $(C_1-C_6)$-alkyl, $(CH_2)_r-C_pF_{2p+1}$, $(C_3-C_6)$cycloalkyl $(C_1-C_2)$-alkyl-$(C_3-C_5)$-cycloalkyl or $(C_2-C_6)$-alkenyl;
  r is zero, 1, 2, 3, 4 or 5;
  p is 1, 2, 3, 4, 5 or 6;
R(2) is NR(3)R(4);
  R(3) and R(4) together are
    a $(CH_2)_{2-7}$ chain in which, for a chain length of 4 to 7, one of the $CH_2$ groups can be replaced by oxygen, sulfur or NR(5), where there must be at least one $CH_2$ group between the N atom of the NR(3)R(4) and the oxygen, sulfur or NR(5);
or
  R(3), R(4) and R(5), independently of one another, are hydrogen, $(C_1-C_6)$-alkyl, $(CH_2)_r-C_pF_{2p+1}$, $(C_3-C_6)$-cycloalkyl, $(C_1-C_2)$-alkyl-$(C_3-C_5)$-cycloalkyl or $(C_2-C6)$-alkenyl;
    r is zero, 1, 2, 3, 4 or 5;
    p is 1, 2, 3, 4, 5 or 6;
E is oxygen or sulfur;
Y is a hydrocarbon chain of the formula $-[CR(6)_2]_n-$;
  R(6) is hydrogen or $(C_1-C_2)$-alkyl;
  n is 1, 2, 3 or 4;
X is hydrogen, F, Cl, Br, I or $(C_1-C_6)$-alkyl; and
Z is F, Cl, Br, I, $NO_2$, $(C_1-C_4)$-alkoxy or $(C_1-C_4)$ alkyl.

If not stated otherwise, the term alkyl describes straight-chain or branched, saturated hydrocarbon radicals. The cycloalkyl radical can additionally carry alkyl substituents.

As halogen substituents, the elements fluorine, chlorine, bromine and iodine can be employed. The carbon atoms of the alkyl side chain Y can be asymmetrically substituted. The invention in this case includes compounds of one or the other enantiomer and of a racemic mixture or mixtures of the antipodes in different proportions. Compounds having two to four centers of chirality can furthermore occur in the alkyl side chain Y. In this case, the invention includes both the individual antipodes per se, and a mixture of the enantiomers or diastereomers in different proportions, and also the associated meso compounds or mixtures of meso compounds, the enantiomers or diastereomers.

Similar sulfonylureas are disclosed in German Offenlegungsschrift No. 2,413,514 and German Patent No. 1,518,874. German Offenlegungsschrift No 2,413,514 exclusively describes blood sugar-conditioning substances with p-substitution in the central phenyl group. References to amino substituents are not found.

In both patent publications, the hypoglycemic action of the sulfonylureas is described. The prototype of hypoglycemic sulfonylureas of this type is glibenclamide, which is used therapeutically as an agent for the treatment of diabetes mellitus and serves in science as a much-esteemed tool for research into so-called ATP-sensitive potassium channels. In addition to its hypotensive action, glibenclamide additionally has other actions which to date still cannot be employed therapeutically, but which are all attributed to blockade of precisely these ATP-sensitive potassium channels. These include, in particular, an antifibrillatory action on the heart. In the treatment of ventricular fibrillation or its preliminary stages, however, a simultaneous blood sugar decrease would be undesired or even dangerous, as it can further aggravate the condition of the patient.

It was therefore an object of the present invention to synthesize compounds which have an equally good cardiac action as glibenclamide, but which do not affect the blood sugar or affect it slightly less in cardioactive doses or concentrations than glibenclamide.

Suitable experimental animals for the detection of actions of this type are, for example, mice, rats, guinea-pigs, rabbits, dogs, monkeys or pigs.

The compounds I are used as pharmaceutical active compounds in human and veterinary medicine. They can also be used as intermediates for the preparation of further pharmaceutical active compounds.

Preferred compounds I are those in which:
R(1) is hydrogen, $(C_1-C_4)$-alkyl, $C_pF_{2p+1}$, $(C_3-C_5)$-cycloalkyl, $CH_2-(C_3-C_5)$-cycloalkyl or $(C_3-C_4)$-alkenyl;
  p is 1, 2 or 3;
R(2) is NR(3)R(4);
  (R3) and R(4) together are
    a $(CH_2)_{2-7}$ chain in which, for a chain length of 4 to 7 one of the $CH_2$ groups can be replaced by oxygen, sulfur or NR(5), where there must be at least one $CH_2$ group between the N atom of the NR(3)R(4) and the oxygen, sulfur or NR(5);
or
  R(3), R(4) and R(5), independently of one another, are hydrogen, $(C_1-C_6)$-alkyl, $(CH_2)_r-C_pF_{2p+1}$, $(C_3-C_6)$-cycloalkyl, $(C_1-C_2)$-alkyl-$(C_3-C_5)$-cycloalkyl or $(C_2-C_6)$-alkenyl;
    r is zero, 1, 2, 3, 4 or 5;
    p is 1, 2, 3, 4, 5 or 6;
E is oxygen or sulfur;
Y is a hydrocarbon chain of the formula $-[R(6)_2]_n-$;
  (6) is hydrogen or $(C_1-C_2)$-alkyl;
  n is 1, 2, 3 or 4;
X is hydrogen, F, Cl or $(C_1-C4)$-alkyl; and
Z is Cl, F, $(C_1-C_4)$-alkyl or $(C_1-C_4)$-alkoxy.

Particularly preferred compounds I are those in which:
R(1) is hydrogen, $(C_1-C_4)$-alkyl, $(C_3-C_4)$-cycloalkyl or $(C_3-C_4)$-alkenyl;
R(2) is NR(3)R(4),
  R(3) and R(4) together are
    a $(CH_2)_{4-6}$ chain in which a $CH_2$ group can be replaced by oxygen, sulfur or N—R (5), where there must be at least one $CH_2$ group between the N atom of the NR(3)R(4) and the oxygen, sulfur or NR(5),
or
  R(3) and R(4) independently of one another, are $CH_3$, $C_2H_5$, n-propyl, isopropyl or cyclopropyl;

R(5) is hydrogen, $CH_3$ or $C_2H_5$;

E is oxygen or sulfur;

Y is a hydrocarbon chain of the formula $-[CR(6)_2]_n-$,

R(6) is hydrogen or methyl;

n is 2 or 3;

X is hydrogen, Cl, F or $(C_1-C_3)$-alkyl; and

Z is F, Cl or $(C_1-C_3)$-alkoxy.

The compounds I of the present invention are useful pharmaceuticals for the treatment of cardiac arrhythmias of very different origin and for the prevention of sudden heart death caused by arrhythmia and can therefore be used as antiarrhythmics. Examples of arrhythmic disorders of the heart are supraventricular arrhythmias such as, for example, atrial tachycardias, atrial flutter or paroxysmal supraventricular arrhythmias, or ventricular arrhythmias such as ventricular extrasystoles, but in particular life-threatening ventricular tachycardias or the particularly dangerous ventricular fibrillation. They are particularly suitable for those cases in which arrhythmias are a result of constriction of a coronary vessel, such as occur, for example, in angina pectoris or during an acute cardiac infarct or as a chronic result of a cardiac infarct. They are therefore particularly suitable in post-infarct patients for the prevention of sudden heart death. Further syndromes in which arrhythmias of this type and/or sudden heart death caused by arrhythmia play a part are, for example, cardiac insufficiency or cardiac hypertrophy as a result of chronically increased blood pressure.

Moreover, the compounds I can positively affect a decreased contractility of the heart. This can be a disease-related decrease in cardiac contractility, for example in the case of cardiac insufficiency, but also acute cases such as heart failure in the case of the effect of shock. In the case of heart transplantation, the heart can also regain its functional capacity more rapidly and more reliably after the operation has taken place. The same applies to operations on the heart which make necessary temporary shutdown of heart activity by means of cardioplegic solutions, it being possible for the compounds to be used both for the protection of the organs in the donor before and during removal, for the protection of removed organs, for example during treatment with or storage thereof in physiological bath fluids, and also during transfer to the recipient's body.

The invention furthermore relates to a process for the preparation of the compounds I, which comprises (a) reacting aromatic sulfonamides of the formula II or their salts of the formula III

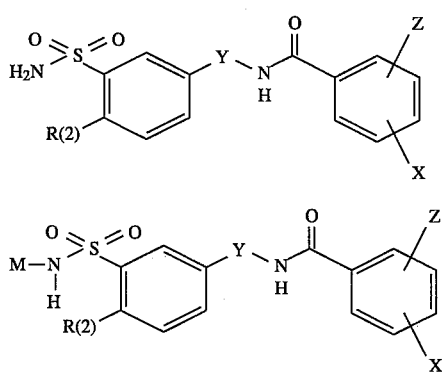

with an R(1)-substituted isocyanate of the formula IV $$R(1)-N=C=O \quad (IV)$$

to give substituted benzenesulfonylureas Ia.

Suitable cations M in the salts of the formula III are alkali metal and alkaline earth metal ions. As an equivalent to the R(1)-substituted isocyanates IV, R(1)-substituted carbamic acid esters, R(1)-substituted carbamoyl halides or R(1)-substituted ureas can be employed.

(b) Unsubstituted benzenesulfonylureas Ia [R (1)=H]

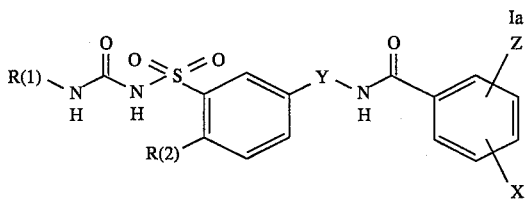

can be prepared by reactions of aromatic benzenesulfonamides of the formula II or their salts III with trialkylsilyl isocyanate or silicon tetraisocyanate and hydrolysis of the primary silicon-substituted benzenesulfonylureas. It is furthermore possible to prepare benzenesulfonamides II or their salts III by reaction with cyanogen halides and hydrolysis of the primarily formed N-cyanosulfonamides with mineral acids at temperatures between 0° and 100° C.

(c) Benzenesulfonylureas Ia

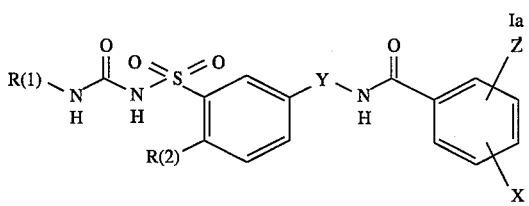

can be prepared from aromatic benzenesulfonamides II or their salts III and R(1)-substituted trichloroacetamides of the formula V

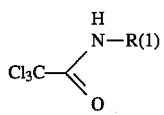

in the presence of a base in an inert solvent according to Synthesis 1987, 734 to 735, at temperatures from 25° to 150° C.

Suitable bases are, for example, alkali metal or alkaline earth metal hydroxides, hydrides, amides or alternatively alkoxides, such as sodium hydroxide, potassium hydroxide, calcium hydroxide, sodium hydride, potassium hydride, calcium hydride, sodium amide, potassium amide, sodium methoxide, sodium ethoxide, potassium methoxide or potassium ethoxide. Suitable inert solvents are ethers such as tetrahydrofuran, dioxane, ethylene glycol dimethyl ether (diglyme), nitriles such as acetonitrile, esters such as ethyl acetate, carboxamides such as dimethylformamide (DMF) or N-methylpyrrolidone (NMP), sulfoxides such as DMSO, sulfones such as sulfolane, hydrocarbons such as benzene, toluene and xylenes. Furthermore, mixtures of these solvents with one another are also suitable.

(d) Benzenesulfonylthioureas Ib

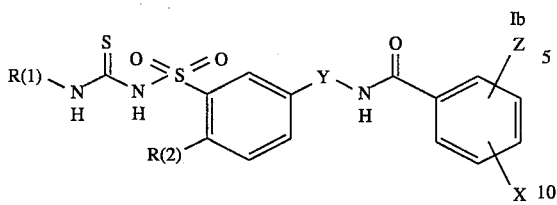

are prepared from benzenesulfonamides II and their salts III and R(1)-substituted thioisocyanates IV

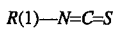   (IV)

(e) Substituted benzenesulfonylureas of the formula Ia can be prepared by rearrangement reactions of benzenesulfonylthioureas of the structure Ib. The replacement of the sulfur atom by an oxygen atom in the appropriately substituted benzenesulfonylthioureas Ib can be achieved, for example, with the aid of oxidants such as hydrogen peroxide, sodium peroxide or nitric acid. Thioureas can also be desulfurized by treatment with phosgene or phosphorus pentachloride. The intermediate compounds obtained are chloroformamidines or carbodiimides which, for example, are converted to the corresponding substituted benzenesulfonylureas Ia by hydrolysis or addition of water. Isothioureas behave as thioureas during desulfurization and can accordingly likewise be used as starting substances for these reactions.

(f) Benzenesulfonylureas Ia can be prepared by reactions of amines of the formula $R(1)—NH_2$ with benzenesulfonyl isocyanates of the formula VII

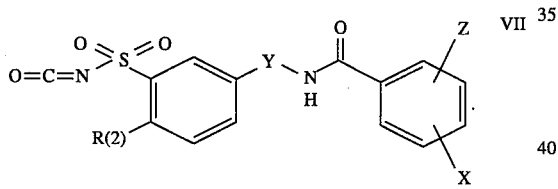

Likewise, amines $R(1)—NH_2$ can be reacted with benzenesulfonylcarbamic acid esters, —carbamoyl halides or benzenesulfonylureas Ia [where R(1)=H] to give the compounds Ia.

(g) Benzenesulfonylthioureas Ib can be prepared by reactions of amines of the formula $R(1)—NH_2$ with benzenesulfonyl isothiocyanates of the formula VIII

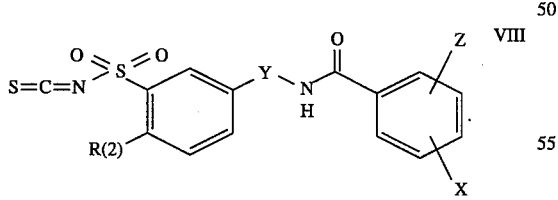

Likewise, amines $R(1)—NH_2$ can be reacted with benzenesulfonylcarbamic acid thioesters or carbamoyl thiohalides to give the compounds Ib.

The compounds I and their physiologically acceptable salts are useful therapeutics, which are suitable not only as antiarrhythmics, but also as prophylaxis in disorders of the cardiovascular system, cardiac insufficiency, heart transplantation or cerebral vascular disorders in humans or mammals (for example monkeys, dogs, mice, rats, rabbits, guinea-pigs and cats).

According to Remmington's Pharmaceutical Science, 17th Edition, 1985, pages 14 to 18, physiologically acceptable salts of the compounds I are understood as meaning compounds of the formula X

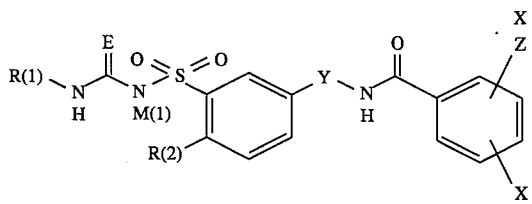

which can be prepared from non-toxic organic and inorganic bases and substituted benzenesulfonylureas I.

Preferred salts here are those in which M(1) in the formula X are sodium, potassium, rubidium, calcium or magnesium ions, as well as the acid addition products of basic amino acids, such as, for example, lysine or arginine.

The starting compounds for the synthesis processes mentioned for the benzenesulfonylureas I are prepared by methods known per se, as are described in the literature (for example in the standard works such as Houben-Weyl, Methoden der Organischen Chemie (Methods of Organic Chemistry), Georg Thieme Verlag, Stuttgart; Organic Reactions, John Wiley & Sons, Inc., New York; as well as in the patent applications given above), to be precise under reaction conditions which are known and suitable for said reactions. Use can also be made in this case of variants which are known per se but not mentioned here in greater detail. If desired, the starting substances can also be formed in situ such that they are not isolated from the reaction mixture, but immediately reacted further.

Scheme 1

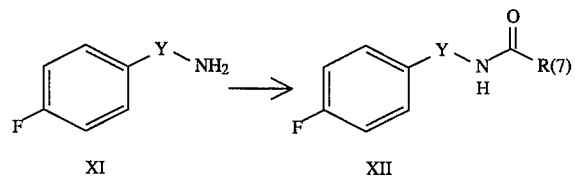

R(7) is $CB_3$,

B is Cl or F, $O—(C_1-C_6)$-alkyl or $O—CH_2C_6H_5$.

Fluorine-substituted phenylalkylamines can thus be acylated according to Scheme 1. Suitable compounds for the acylation of amino groups are expediently the alkyl esters, halides (e.g. chlorides or bromides) or anhydrides of carboxylic acids of the formula

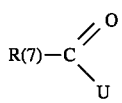

where R(7) is defined in Scheme 1 and U is a leaving group such as halide, $(C_1-C_4)$-alkoxy, trihaloacetate or $(C_1-C_4)$-carboxylate.

The amines XII acylated according to Scheme 1 can be converted in a known manner according to Scheme 2

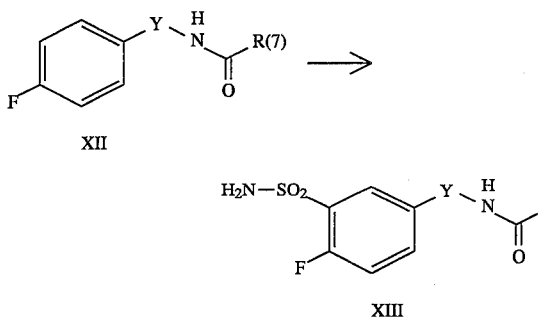

to the sulfonamides XIII. The sulfonamides XIII are prepared by methods known per se, to be precise under reaction conditions which are known and suitable for said reactions. Use can be made in this case of variants known per se, but not mentioned here in greater detail. If desired, the syntheses can be carried out in one, two or more steps. Processes are particularly preferred in which the acylated amine XII is converted by electrophilic reagents in the presence or absence of inert solvents at temperatures from −10° to 120° C., preferably from 0° to 100° C., to aromatic sulfonic acids and their derivatives such as, for example, sulfonyl halides. For example, sulfonations using sulfuric acid or oleum, halosulfonations using halosulfonic acids, reactions with sulfuryl halides in the presence of anhydrous metal halides or thionyl halides in the presence of anhydrous metal halides with subsequent oxidations carried out in a known manner to give aromatic sulfonyl chlorides, can be carried out. If sulfonic acids are the primary reaction products, these can either be converted directly or by treatment with tertiary amines, such as, for example, pyridine or trialkylamines, or with alkali metal or alkaline earth metal hydroxides or reagents which form these basic compounds in situ, to sulfonyl halides in a known manner by acid halides such as, for example, phosphorus trihalides, phosphorus pentahalides, phosphorus oxychlorides, thionyl halides or oxalyl halides. The conversion of the sulfonic acid derivatives to sulfonamides is carried out in a manner known from the literature, preferably sulfonyl chlorides are reacted with aqueous ammonia in inert solvents at temperatures from 0° to 100° C.

The sulfonamides XIII are reacted, according to Scheme 3, with amines of the formula HNR(3)R(4) at temperatures from 25° to 160° C. in the presence or absence of inert solvents to give the amino-substituted sulfonamides XIV.

Scheme 3

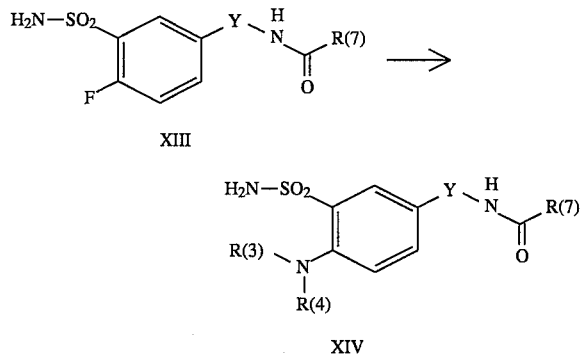

The acyl protective group of the amine XIV can be removed with acids or bases. The associated acid addition salt can be formed by cleavage with aqueous acids or acids in inert solvents. Suitable acids for this reaction are, for example, sulfuric acid, hydrohalic acids, such as hydrochloric acid or hydrobromic acid, phosphoric acids such as orthophosphoric acid, polyphosphoric acid, sulfamic acid, and also organic acids, in particular aliphatic, alicyclic, araliphatic, aromatic or heterocyclic mono- or polybasic carboxylic, sulfonic or sulfuric acids, for example acetic acid, propionic acid, pivalic acid, diethylacetic acid, malonic acid, succinic acid, pimelic acid, fumaric acid, malic acid, lactic acid, tartaric acid, malic acid, benzoic acid, salicylic acid, 2- or 3-phenylpropionic acid, phenylacetic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid.

The basic cleavage of the acylated amine of the formula XIV can be carried out in aqueous or inert solvents. Suitable bases are, for exaanple, alkali metal or alkaline earth metal hydroxides, or alternatively alkoxides, such as sodium hydroxide, potassium hydroxide, calcium hydroxide, sodium methoxide, sodium ethoxide, potassium methoxide or potassium ethoxide, as well as reductants such as $NaBH_4$ and other boranes or borohydrides.

As mentioned above, the aromatic benzenesulfonamides of the formula II are prepared from the sulfonamide-substituted amines or their acid addition compounds prepared in this way. Depending on the nature of the members R(1), R(2), R(3), R(4), R(5), R(6), E, X, Y and Z, in individual cases one or the other of said processes will be unsuitable for the preparation of the compounds I or at least make precautions necessary for the protection of active groups. Cases of this type can be recognized easily by the person skilled in the art, and it should present no difficulties in such cases to use another synthesis route successfully.

The compounds I can have one or more chiral centers. They can therefore be obtained in their preparation as racemates or, if optically active starting substances are used, alternatively in optically active form. If the compounds have two or more chiral centers, they can then be obtained in the synthesis as mixtures of racemates from which the individual isomers can be obtained in pure form, for example by recrystallizing from inert solvents. If desired, racemates obtained can be resolved into their enantiomers mechanically or chemically by methods known per se. Thus, diastereomers can be formed from the racemate by reaction with an optically active resolving agent. Suitable resolving agents for basic compounds are, for example, optically active acids, such as the R- or R,R- and S- or S,S-forms of tartaric acid, dibenzoyltartaric acid, diacetyltartaric acid, camphorsulfonic acid, mandelic acid, malic acid or lactic acid. Carbinols can also be amidated with the aid of chiral acylating reagents, for example R- or S-α-methylbenzyl isocyanate and then resolved. The various forms of the diastereomers can be separated in a known manner, for example by fractional crystallization, and the enantiomers of the formula I can be set free from the diastereomers in a manner known per se. Resolution of enantiomers is also carried out by chromatography on optically active support materials.

The compounds I according to the invention and their physiologically acceptable salts can be used for the production of pharmaceutical preparations. In this case, they can be brought into a suitable dosage form, together with at least one solid or liquid excipient or auxiliary, on their own or in combination with other cardiovascular pharmaceuticals such as, for example, calcium antagonists, NO donors or ACE inhibitors. These preparations can be used as pharmaceuticals in human or veterinary medicine. Possible excipients are organic or inorganic substances which are suitable for enteral (for example oral), parenteral, such as, for example, intravenous administration, or topical applications and do not react with the novel compounds, for example water, vegetable oils, benzyl alcohols, polyethylene glycols, glycerol triacetate, gelatin, carbohydrates such as lactose or starch, magnesium stearate, talc, lanolin or petroleum jelly. For oral administration, tablets, sugar-coated tablets, capsules, syrups, juices or drops are used in particular, for rectal administration solutions, preferably oily or aqueous solutions, and also suspensions, emulsions or implants are used, for topical administration, ointments, creams, pastes, lotions, gels, sprays, foams, aerosols, solutions (for example in alcohols, such as ethanol or isopropanol, 1,2-propanediol or mixtures thereof with one another or with water) or powders are used. The novel compounds can also be lyophilized and the lyophilizates obtained used, for example for the production of injection preparations. Liposomal preparations are also particularly suitable for topical application. The pharmaceutical preparations contain stabilizers and/or wetting agents, emulsifiers, salts and/or auxiliaries such as lubricants, preservatives, salts for influencing the osmotic pressure, buffer substances, colorants and flavorings and/or aromatizers. If desired, they can also contain one or more other active compounds, for example one or more vitamins.

The doses which are necessary for the treatment of cardiac arrhythmias using the compounds I depend on whether the therapy is acute or prophylactic. Normally, a dose range of at least about 0.1 mg, preferably about 1 mg, in particular at least about 10 mg, up to at most 100 mg, preferably at most 50 mg per kg and day is needed if prophylaxis is carried out. A dose range of 1 to 10 mg per kg and day is very particularly preferred. In this case, the dose can be divided into up to four individual doses as an oral or parenteral individual dose. If acute cases of cardiac arrhythmias are being treated, for example in an intensive care unit, parenteral administration can be advantageous. A preferred dose range in critical situations may then be 10 to 100 mg and is administered, for example, as an intravenous continuous infusion.

According to the invention, in addition to the compounds described in the exemplary embodiments, the compounds I assembled in the following table can be obtained:

(1) 2-Methoxy-5- fluoro-N-{5-[-1-sulfonylamino-N-(methylamlnothiocarbonyl)-2-(4-morpholino)phenyl] ethyl}benzamide,
(2) 2-methoxy-5-chloro-N-{5-[-1-sulfonylamino-N-(methylaminocarbonyl)-2-(4-morpholino)phenyl]ethyl}-benzamide,
(3) 2-methoxy-5-chloro-N-{5-[-1-sulfonylamino-N-(methylaminocarbonyl)-2-(4-morpholino)phenyl]-(3-propyl)}benzamide,
(4) 2-methoxy-5-chloro-N-{5-[-1-sulfonylamino-N-(methylaminocarbonyl)-2-(4-thiomorpholino)phenyl] ethyl}benzamide,
(5) 2-methoxy-5-fluoro-N-{5-[1-sulfonylamino-N-(methylaminothiocarbonyl)-2-(4-thiomorpholino)phenyl] ethyl}benzamide,
(6) 2-methoxy-5-chloro-N-{5-[-1-sulfonylamino-N-(methylaminocarbonyl)-2-(4-thiomorpholino)phenyl] ethyl}benzamide,
(7) 2-methoxy-5-fluoro-N-{5-[-1-sulfonylamino-N-(methylaminocarbonyl)-2-(4-N-methylpiperazyl)phenyl] ethyl}benzamide,
(8) 2-methoxy-5-chloro-N-{5-[-1-sulfonylamino-N-(methylaminothiocarbonyl)-2-(4-N-methylpiperazyl)phenyl] ethyl}benzamide,
(9) 2-methoxy-5-chloro-N-{5-[-1-sulfonylamino-N-(methylaminocarbonyl)-2-(N,N-dimethylamino)phenyl] ethyl}benzamide,
(10) 2-methoxy-5-fluoro-N-{5-[-1-sulfonylamino-N-(methylaminothiocarbonyl)-2-(N,N -dimethylamino)phenyl] ethyl)benzamide,
(11) 2-methoxy-5-chloro-N-{5-[-1-sulfonylamino-N-(methylaminocarbonyl)-2-(N,N-diethylamino)phenyl] ethyl}benzamide,
(12) 2-methoxy-5-chloro-N-{5-[-1-sulfonylamino-N-(methylaminocarbonyl)-2-(1-pyrrolidyl)phenyl] ethyl}benzamide.

List for R(2) =

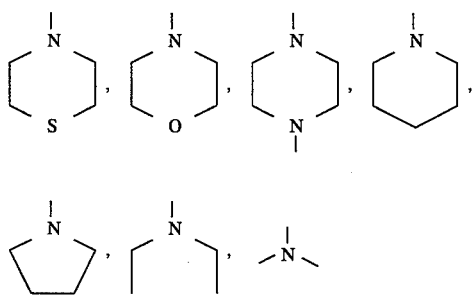

EXAMPLE 1

2-Methoxy-5-chloro-N-{5-[1-sulfonylamino-N-(methylaminothiocarbonyl)-2-(4-morpholino)phenyl] ethyl}benzamide

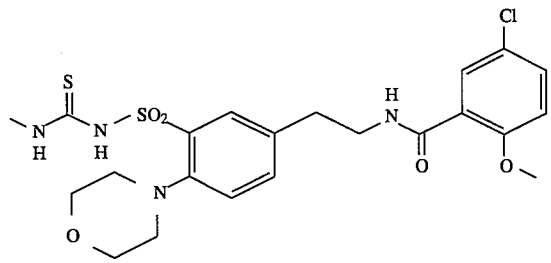

0.45 g (1.0 mmol) of 2-methoxy-5-chloro-N-[5-(1-sulfonylamino-2-(4-morpholino)phenyl)ethyl]benzamide is dissolved in 5 ml of dry DMF under argon and treated at 0° C. with 42 mg of sodium hydride (60% strength dispersion in white oil). The cooling bath is removed and the reaction mixture is stirred at room temperature for 30 minutes. 0.10 g of methyl isothiocyanate is introduced into the solution of the sodium sulfonamide and it is stirred at room temperature for 5 hours and at 70° C. for 1 hour. After cooling, the reaction mixture is poured into 50 ml of 0.5N hydrochloric acid. The precipitated product is filtered off with suction and dried. Yield: 96%, m.p.: 195° to 196° C.

Preparation of the Starting Compound 1.39 g (10.0 mmol) of 4-fluoro-β-phenylethylamine are dissolved in 40 ml of pyridine, treated with a spatula tipful of dimethylaminopyridine and with a solution of 2.15 g (10.5 mmol) of 2-methoxy-5-chlorobenzoyl chloride. The reaction mixture is poured into cold dilute hydrochloric acid, and the precipitated product is filtered off with suction and dried. 4-Fluoro-β-phenylethyl-(2-methoxy-5-chlorobenzamide) is obtained as colorless crystals of melting point 85° C. The benzamide thus obtained is introduced into cold chlorosulfonic acid. After reaction is complete, the reaction mixture is poured onto ice, and the precipitate is filtered off with suction (melting point of the sulfonyl chloride: 118° C.) and dissolved in acetone. This solution is treated with excess, concentrated aqueous ammonia and, after the exothermic reaction has subsided, concentrated to a third of the original volume. The 2-methoxy-5-chloro-N-[5-(1-sulfonylamino-2-fluorophenyl)ethyl]benzamide forms colorless crystals which melt at 203° C. Heating of 2-methoxy-5-chloro-N-[5-(1-sulfonylamino-2-fluorophenyl)ethyl]benzamide in excess morpholine under reflux for three hours yields 2-methoxy-5-chloro-N-[5-(1-sulfonylamino-2-(4-morpholino)phenyl)ethyl]benzamide, which is isolated by column chromatography (silica gel 60, heptane/ethyl acetate gradient of 2:1 to 4:1). The product melts at 236° C.

EXAMPLE 2

2-Methoxy-5-chloro-N-{5-[1-sulfonylamino-N-(methylaminothiocarbonyl)-2-(1-piperidyl)phenyl]ethyl}benzamide

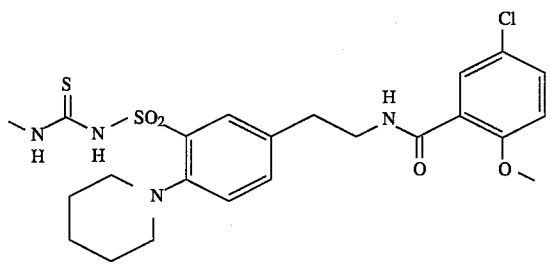

0.45 g (1.0 mmol of 2-methoxy-4-chloro-N-[5-(1-sulfonylamino-2-(1-piperidyl)phenyl)ethyl]benzamide is dissolved in 5 ml of dry DMF under argon and treated at 0° C. with 42 mg of sodium hydride (60% strength dispersion in white oil). The cooling bath is removed and the reaction mixture is stirred at room temperature for 30 minutes. To dissolve the sodium sulfonamide, 0.10 g of methyl isothiocyanate is added and the mixture is stirred at room temperature for 5 hours and at 70° C. for 1 hour. After cooling, it is poured into 50 ml of 0.5N hydrochloric acid. The precipitated product is filtered off with suction and dried.

Yield: 95%, m.p.: 90° C.

Preparation of the Starting Compound

A solution of 2-methoxy-5-chloro-N-[5-(1-sulfonylamino-2-fluorophenyl)ethyl]benzamide in excess piperidine is heated under reflux for 4 hours. After removal of the solvent by distillation in vacuo, 2-methoxy-5-chloro-N-[5-(1-sulfonylamino-2-(1-piperidyl)phenyl)ethyl]benzamide can be isolated by column chromatography (silica gel 60, heptane/ethyl acetate gradient of 2:1 to 4:1) as colorless crystals of melting point 225° C.

Pharmacological Data

The therapeutic properties of the compounds I can be detected using the following models:

(1) Action potential duration on the papillary muscle of the guinea-pig:
(a) Introduction ATP deficiency states, as are observed during ischemia in the cardiac muscle cell, lead to a reduction of the action potential duration. They count as one of the causes of so-called reentry arrhythmias, which can cause sudden heart death. The opening of ATP-sensitive K channels by the reduction of ATP counts as causal here.

(b) Method

To measure the action potential, a standard microelectrode technique is employed. For this, guinea-pigs of both sexes are killed by a blow to the head, the hearts are removed, and the papillary muscles are separated out and suspended in an organ bath. The organ bath is irrigated with Ringer solution (0.9% NaCl, 0.048% KCl, 0,024% $CaCl_2$, 0.02% $NaHCO_3$ and 0.1% glucose) and aerated with a mixture of 95% oxygen and 5% carbon dioxide at a temperature of 36° C. The muscle is stimulated by means of an electrode using square-wave impulses of 1 V and 1 ms duration and a frequency of 2 Hz. The action potential is derived and recorded by means of a glass microelectrode inserted intracellularly, which is filled with 3 mmol KCl solution. The substances to be tested were added to the Ringer solution in a concentration of $2.2 \cdot 10^{-5}$ mol per liter. The action potential is shown amplified on an oscilloscope using an amplifier from Hugo Sachs. The duration of the action potential is determined at a degree of repolarization of 95% ($APD_{95}$). Action potential reductions are produced either by addition of a 1 μM solution of the potassium channel opener rilmakalim (Hoe 234) [W. Linz, E. Klaus, U. Albus, R. H. A. Becker, D. Mania, H. C. Englert, B. A. Schökens, Arzneimittelforschung/Drug Research, Volume 42 (II), 1992, pp. 1180 to 1185] or by addition of 2-deoxyglucose (DEO). In experimental physiology, ATP deficiency states are produced by 2-deoxyglucose by blockade of glucose metabolism. The action potential-reducing effect of these substances was prevented or reduced by the simultaneous addition of the test substances. Test substances were added to the bath solution as stock solutions in propanediol. The values indicated relate to measurements 30 minutes after addition. The $APD_{95}$ in the presence of DEC or rilmakalim and in the absence of the test substance counts as the control.

(c) Results

The following values were measured:

| Measurement | $APD_{95}$-DEO[a] [ms] | $APD_{95}$-rilmakalim [ms] |
| --- | --- | --- |
| Control | <40 | <40 |
| Example 1 | 110 (172) | 121 ± 14 (150) ± 9) |
|  | n = 1 | n = 3 |
| Example 2 | 105 ± 11 (141 ± 4) | 153 ± 15 (158 ± 12) |
|  | n = 3 | n = 3 |

[a]The corresponding blank values are put in brackets after the measurements from n experiments. The blank values are the $APD_{95}$ at the start of the experiment without DEO, rilmakalim and test substance in the Ringer solution.

(2) Membrane potential on isolated β-cells:
(a) Introduction

The mechanism of action of the hypoglycemic sulfonylureas is elucidated in rough terms. The target organ is the β-cells of the pancreas where increased secretion of the hypoglycemic hormone insulin occurs. The release of insulin is controlled by means of the cell membrane potential. Glibenclamide causes a depolarization of the cell mem-

13 brane, which promotes insulin release via an increased influx of calcium ions. The extent of this depolarization of the cell membrane ΔU was determined on RINm5F cells, a pancreas tumor cell line, for a few of the compounds according to the invention. The potency of a compound in this model predicts the extent of the hypoglycemic potential of this compound.

(b) Method

Cell culture of RINm5F cells

RINm5F cells were cultured at 37° C. in RPMI 1640 culture medium (Flow), to which 11 mmol of glucose, 10% (vol/vol) fetal calf-serum, 2 mmol of glutamine and 50 μg/ml of gentamycin were added. For the investigations, the cells were isolated by incubation (about 3 minutes) in a $Ca^{2+}$-free medium which contained 0.25% trypsin and were stored on ice.

Measuring Method

Isolated RINm5F cells were transferred to a Plexiglas chamber on an inverted microscope which is equipped with a differential interference contrast optical system. Under visual control (400-fold magnification), a fire-polished micropipette with an opening diameter of about 1 μm was set up on the cell with the aid of a micromanipulator. By applying a slight reduced pressure in the patch pipette, a high electrical seal was first produced between the glass and cell membrane and then broken by increasing the reduced pressure of the membrane spot under the measuring pipette. In this whole cell configuration, the cell potential was recorded with the aid of a patch clamp amplifier (L/M EPC 7) and measured by applying a voltage ramp to the whole cell current.

Solutions: The patch pipette was filled with KCl solution (in mmol): 140 KCl, 10 NaCl, 1.1 $MgCl_2$, 0.5 EGTA, 1 Mg-ATP, 10 HEPES, pH =7.2, and NaCl solution was in the bath (in mmol): 140 NaCl, 4.7 KCl, 1.1 $MgCl_2$, 2 $CaCl_{12}$, 10 HEPES, pH=7.4. Stock solutions (concentration 100 mmol) in dimethyl sulfoxide (DMSO) and corresponding dilutions in NaCl solution were prepared of the test substances. DMSO on its own had no effect on the cell potential. In order to stabilize the cell potential under control conditions, diazoxide (100 μmol) was added in the bath solution to the openers for ATP-sensitive $K^+$ channels in all experiments. All experiments were carried out at 34°±1° C.

(c) Results (The concentration of the compounds according to the invention in the experiments was $10^{-6}$ mol per liter)

| Measurement | ΔU (mv)[a] |
|---|---|
| Example 1 | 14 (−76) n = 7 |
| Example 2 | 19 (−76) n = 3 |

[a] The corresponding blank values are put in brackets after the measurements from n experiments. The blank values are the cell potentials under diazoxide addition.

14

We claim:
1. A substituted benzenesulfonylurea or -thiourea I

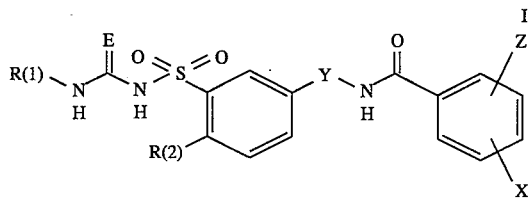

in which:
R(1) is hydrogen, $(C_1–C_6)$ alkyl, $(CH_2)_r$—$C_pF_{2p+1}$, $(C_3–C_6)$-cycloalkyl, $(C_1–C_2)$-alkyl-$(C_3–C_5)$-cycloalkyl or $(C_2–C_6)$-alkenyl;
  r is zero, 1, 2, 3, 4 or 5;
  p is 1, 2, 3, 4, 5 or 6;
R(2) is NR(3)R(4),
  R(3) and R(4) together are
    a $(CH_2)_{2–7}$ chain in which, for a chain length of 4 to 7, one of the $CH_2$ group can be replaced by oxygen, sulfur or NR(5), where there must be at least one $CH_2$ group between the N atom of the NR(3)R(4) and the oxygen, sulfur or NR(5);
or
  R(3), R(4) and R(5), independently of one another, are hydrogen, $(C_1–C_6)$ alkyl, $(CH_2)_r$—$C_pF_{2p+1}$, $(C_3–C_6)$-cycloalkyl, $(C_1–C_2)$-alkyl-$(C_3–C_5)$-cycloalkyl or $(C_2–C_6)$-alkenyl;
    r is zero, 1, 2, 3, 4 or 5;
    p is 1, 2, 3, 4, 5 or 6;
E is oxygen or sulfur;
Y is a hydrocarbon chain of the formula —$[CR(6)_2]_n$—;
  R(6) is hydrocarbon or $(C_1–C_2)$-alkyl;
  n is 1, 2, 3 or 4;
X is hydrogen, F, Cl, Br, I or $(C_1–C_6)$-alkyl; and
Z is F, Cl, Br, I, $NO_2$, $(C_1–C_4)$-alkoxy or $(C_1–C_4)$; alkyl, or the physiologically acceptable salt thereof.

2. A compound of the formula I as claimed in claim 1, wherein:
R (1) is hydrogen, $(C_1–C_4)$-alkyl, $C_pF_{2p+1}$, $(C_3–C_5)$-cycloalkyl, $CH_2$—$(C_3–C_5)$-cycloalkyl or $(C_3–C_4)$-alkenyl;
  p is 1, 2 or 3,
R(2) is NR(3)R(4),
  R(3) and R(4) together are
    a $(CH_2)_{2–7}$ chain in which, for a chain length of 4 to 7, one of the $CH_2$ groups can be replaced by oxygen, sulfur or NR(5), where there must be at least one $CH_2$ group between the N atom of the NR(3)R(4) and the oxygen, sulfur or NR(5);
or
  R(3), R(4) and R(5), independently of one another, are hydrogen, $(C_1–C_6)$-alkyl, $(CH_2)_r C_pF_{2p+1}$, $(C_3–C_6)$-cycloalkyl, $(C_1–C_2)$-alkyl-$(C_3–C_5)$-cycloalkyl or $(C_2–C_6)$-alkenyl;
    r is zero, 1, 2, 3, 4 or 5;
    p is 1, 2, 3, 4, 5 or 6;
E is oxygen or sulfur,
Y is a hydrocarbon chain of the formula —$[R(6)_2]_n$—,
  R(6) is hydrogen or $(C_1–C_2)$-alkyl;
  n is 1, 2, 3 or 4;
X is hydrogen, F, Cl or $(C_1–C_4)$-alkyl; and
Z is Cl, F, $(C_1–C_4)$-alkyl or $(C_1–C_4)$-alkoxy.

3. A compound of the formula I as claimed in claim 1, wherein:
R(1) is hydrogen, $(C_1–C_4)$-alkyl, $(C_3–C_4)$-cycloalkyl or $(C_3-C_4)$-alkenyl;

R(2) is NR(3)R(4);

R(3) and R(4) together are a $(CH_2)_{4-6}$ chain in which a $CH_2$ group can be replaced by oxygen, sulfur or N–R(5), where there must be at least one $CH_2$ group between the N atom of the NR(3)R(4) and the oxygen, sulfur or NR(5);

or

R(3) and R(4), independently of one another, are $CH_3$, $C_2H_5$, n-propyl, isopropyl or cyclopropyl, R(5) is hydrogen, $CH_3$ or $C_2H_5$;

E is oxygen or sulfur;

Y is a hydrocarbon chain of the formula $-[CR(6)_2]_n-$;

R(6) is hydrogen or methyl;

n is 2 or 3;

X is hydrogen, Cl, F or $(C_1-C_3)$-alkyl; and

Z is F, Cl or $(C_1-C_3)$-alkoxy.

4. A pharmaceutical preparation which contains an effective amount of a compound I as claimed in claim 1.

5. A method for treating arrhythmias and infarct and for cardioprotection, which comprises administering an effective amount of a compound I as claimed in claim 1, which is mixed with customary additives and brought into a suitable administration form.

6. A method for the treatment or prophylaxis of ischemic conditions of the heart, comprising administering an amount of a compound I as claimed in claim 1 effective for said treatment or prophylaxis, with or without a pharmaceutically acceptable excipient.

* * * * *

UNITED STATES PATENT AND TRADEMARK OFFICE
CERTIFICATE OF CORRECTION

PATENT NO. : 5,476,850
DATED : December 19, 1995
INVENTOR(S) : Heinrich ENGLERT et al.

It is certified that error appears in the above-indentified patent and that said Letters Patent is hereby corrected as shown below:

Claim 1, column 14, line 13, "$(C_1-C_6)$ alkyl" should read --$(C_1-C_6)$-alkyl--.

Claim 1, column 14, line 27, "$(C_1-C_6)$ alkyl" should read --$(C_1-C_6)$-alkyl--.

Claim 1, column 14, line 37, "$(C_1-C_4)$;alkyl" should read --$(C_1-C_4)$-alkyl--.

Signed and Sealed this

Thirteenth Day of August, 1996

Attest:

BRUCE LEHMAN

*Attesting Officer*      *Commissioner of Patents and Trademarks*